(12) United States Patent
Arnett et al.

(10) Patent No.: US 10,526,628 B2
(45) Date of Patent: Jan. 7, 2020

(54) ENZYME-MEDIATED ASSIMILATION OF DNA-FUNCTIONALIZED SINGLE-WALLED CARBON NANOTUBES (SWNTS)

(75) Inventors: Clint M. Arnett, Mahomet, IL (US); Charles P. Marsh, Urbana, IL (US); Jae Hee Han, Gyeonggi-do (KR); Michael S. Strano, Lexington, MA (US); Charles R. Welch, Vicksburg, MS (US); Thomas A. Carlson, Champaign, IL (US)

(73) Assignee: UNITED STATES OF AMERICA AS REPRESENTED BY THE SECRETARY OF THE ARMY, Alexandria, VA (US)

( * ) Notice: Subject to any disclaimer, the term of this patent is extended or adjusted under 35 U.S.C. 154(b) by 555 days.

(21) Appl. No.: 13/267,002

(22) Filed: Oct. 6, 2011

(65) Prior Publication Data
US 2015/0050208 A1  Feb. 19, 2015

Related U.S. Application Data

(60) Provisional application No. 61/390,233, filed on Oct. 6, 2010.

(51) Int. Cl.
*C01B 32/174* (2017.01)
*C12P 19/34* (2006.01)

(52) U.S. Cl.
CPC ............ *C12P 19/34* (2013.01); *C01B 32/174* (2017.08); *C01B 2202/02* (2013.01)

(58) Field of Classification Search
CPC .............. C01B 31/022; C01B 31/0253; C01B 31/0273; C01B 32/147; C01B 2202/02; B82Y 30/00

USPC ...... 423/447.1; 977/742, 746, 747, 750, 753
See application file for complete search history.

(56) References Cited

U.S. PATENT DOCUMENTS

| | | |
|---|---|---|
| 7,566,749 B2 | 7/2009 | Fischer et al. |
| 7,897,209 B2 | 3/2011 | Shibuya et al. |
| 7,910,650 B2 | 3/2011 | Fischer et al. |
| 2007/0280876 A1 | 12/2007 | Tour et al. |
| 2008/0134942 A1 | 6/2008 | Brenner et al. |
| 2008/0213162 A1 | 9/2008 | Smalley et al. |
| 2008/0233402 A1 | 9/2008 | Carlson et al. |
| 2009/0232965 A1 | 9/2009 | Hata et al. |
| 2010/0173153 A1 | 7/2010 | Hatta et al. |
| 2010/0203316 A1 | 8/2010 | Hata et al. |
| 2010/0308279 A1 | 12/2010 | Zhou et al. |
| 2011/0008617 A1 | 1/2011 | Hata et al. |

(Continued)

OTHER PUBLICATIONS

Martin, Willis, Wusheng Zhu, and Goran Krilov. "Simulation Study of Noncovalent Hybridization of Carbon Nanotubes by Single-Stranded DNA in Water" The Journal of Physical Chemistry B 112.50 (2008): 16076-16089.*

(Continued)

*Primary Examiner* — Richard M Rump
(74) *Attorney, Agent, or Firm* — Brian C. Jones

(57) ABSTRACT

Select embodiments of the present invention employ biological means to direct assemble CNT-based nanostructures, allowing for scaling to macrostructures for manufacture. In select embodiments of the present invention, a method is provided for assembling DNA-functionalized SWNTs by phosphodiester bonding catalyzed by ssDNA-ligase to form macroscopic CNT aggregates.

7 Claims, 5 Drawing Sheets

(56) References Cited

U.S. PATENT DOCUMENTS

2011/0116995 A1    5/2011  Shibuya et al.
2011/0133133 A1    6/2011  Fischer et al.

OTHER PUBLICATIONS

O'Neill, Patrick, et al. "Sturdier DNA nanotubes via ligation." Nano letters 6.7 (2006): 1379-1383.*

Chen, Yi, et al. "DNA-directed assembly of single-wall carbon nanotubes." Journal of the American Chemical Society 129.28 (2007): 8696-8697.*

Yarotski, Dzmitry A., et al. "Scanning tunneling microscopy of DNA-wrapped carbon nanotubes." Nano letters 9.1 (2008): 12-17.*

Arnett et al., Enzyme-Mediated Assimilation of DNA-Functionalized Single-Walled Carbon Nanotubes (SWNT), American Chemical Society, Revised (unpublished) manuscript, Nov. 23, 2009.

Babic et al., Suitability of CNTs grown by CVD for Electric Devices, Instit fur Physik, Universitat Basel, Basel, Switzerland, undated (pre-2009).

* cited by examiner

𝓐

𝓑

ENZYME-MEDIATED ASSIMILATION OF DNA-FUNCTIONALIZED SINGLE-WALLED CARBON NANOTUBES (SWNTS)

RELATED APPLICATIONS

Under 35 U.S.C. § 119(e)(1), this application claims the benefit of prior U.S. Provisional Patent Application No. 61/390,233, Enzyme-Mediated Assimilation of DNA-Functionalized Single-Walled Carbon Nanotubes (SWNTS), by Marsh et al., filed Oct. 6, 2010, incorporated herein by reference.

STATEMENT OF GOVERNMENT INTEREST

Under paragraph 1(a) of Executive Order 10096, the conditions under which this invention was made entitle the Government of the United States, as represented by the Secretary of the Army, to an undivided interest therein on any patent granted thereon by the United States. This and related patents are available for licensing to qualified licensees. Please contact Bea Shahin at 217 373-7234.

BACKGROUND

Since the discovery of single-walled carbon nanotubes (SWNTs), there has been interest in exploiting them. Iijima, S., *Helical Microtubules of Graphitic Carbon*, Nature 354 (6348), 56-58, (1991). Because of their unique characteristics, SWNTs hold potential for use in many industries. Dresselhaus, M. S. et al., *Philos. Trans. R. Soc. London*, 362, 2065, (2004). On the molecular level, carbon nanotubes (CNTs) are the strongest molecules known. Li, Q., et al., *Adv. Mater.*, 18, 3160, (2006). CNTs are a hundred times stronger than high-strength steel, at a tenth of the weight and have a Young's modulus approximately five times that of hardened steel. Haskins, R. S., et al., *J. Chem. Phys.* 127, 074708, (2007).

Contingent on chirality, SWNTs can be either metallic or semiconducting. Metallic nanotubes may conduct electric current densities 1000 times greater than copper can. Hong, S. and S. Myung, *Nat. Nanotechnol.* 2, 207, (2007). CNTs are excellent thermal conductors. Biercuk et al., *Appl. Phys. Lett.* 80, 2767, (2002). These unique physiochemical properties hold promise for use in structural, mechanical, chemical, and electrical applications. However, low aqueous solubility and intrinsic difficulty in proficiently aligning CNTs have limited their use.

Low solubility may be overcome by covalent chemical modifications. These processes may adversely affect physical and electrochemical properties of CNTs. Haung, W., et al., *Langmuir* 19, 7084, (2003); Liu, P., *Eur. Polym. J.*, 41, 2693, (2005). Biological molecules, bonding non-covalently, offer less invasive modification and are used both to separate and purify CNTs. Zheng et al. have demonstrated the intrinsic ability of single-stranded DNA (ssDNA) to bind and disperse SWNT bundles in aqueous solution. Zheng, M. et al., *Nat. Mater.* 2, 338, (2003a). One theory is that π bonds are formed between the graphene surface and the hydrophobic base pairs of the DNA, resulting in a helical wrapping of ssDNA around the CNT. The hydrophilic phosphate backbone of the DNA remains exposed, causing electrostatic stabilization in water. After being solubilized, SWNTs can be separated and purified on the basis of size and chirality by ion exchange chromatography or gradient centrifugation. Zheng (2003a); Arnold, M. S. et al., *Nat. Nanotechnol.* 1, 60, (2006); Huang, X., et al., *Anal. Chem.* 77, 6225, (2005); Lustig, S. R., et al., *J. Phys. Chem. B*109, 2559, (2005); Zheng, M., et al., *Science* 302, 1545, (2003). Creating pure soluble SWNTs is necessary in extending their potential.

Few efforts have demonstrated how to assemble CNTs, particularly using biological means. The use of DNA to assemble CNTs into nano-devices has attracted attention because of the recognition specificity of the DNA molecule. RecA-based motifs used DNA to localize CNTs to form nano-wires and transistors. Hazani, M., et al., *Chem. Phys. Lett.* 391, 389, (2004); Keren, K., et al., *Science* 302, 1380, (2003). Additionally, nucleic acid hybridizations joined DNA-functionalized CNTs having complementary sequences. Li, Y., et al., *Angew. Chem., Int. Ed.* 46, 7481, (2007); Li, S., et al., *J. Am. Chem. Soc.* 127, 14, (2005). Exploiting biologically-based assembly motifs provides for building higher-order nanostructures with precise control.

Select embodiments of the present invention comprise a novel method for assembling DNA-functionalized SWNTs by phosphodiester bonding catalyzed by ssDNA-ligase to form macroscopic CNT aggregates. Exploiting biological means such as these to direct assemble CNT-based nanostructures allows for scaling to manufacture.

DETAILED DESCRIPTION

Figure 1:
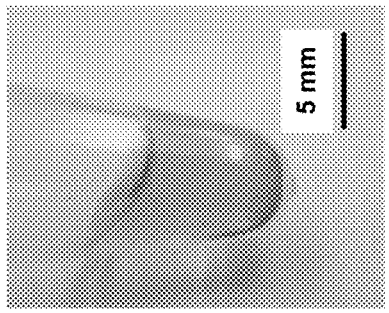
FIG. 1A is a photograph of enzyme-mediated aggregate formation of SWNTs in 1.5 mL micro-centrifuge tubes with ligase added.
FIG. 1B is a light microscopy 10× magnification image of a ligase-amended sample.
FIG. 1C is a photograph of enzyme-mediated aggregate formation of SWNTs in 1.5 mL micro-centrifuge tubes without ligase added.
FIG. 1D is a light microscopy 50× magnification image of an un-amended control (no ligase).
FIG. 1E is a photograph of enzyme-mediated aggregate formation of SWNTs in 1.5 mL micro-centrifuge tubes with deoxyribonuclease (DNase I) added.
FIG. 1F is a light microscopy 50× magnification image of a ligated sample after endonuclease amendment.
Figure 1:
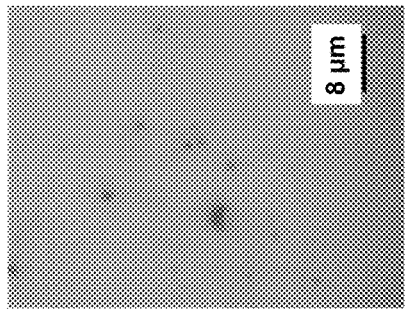
Figure 1:
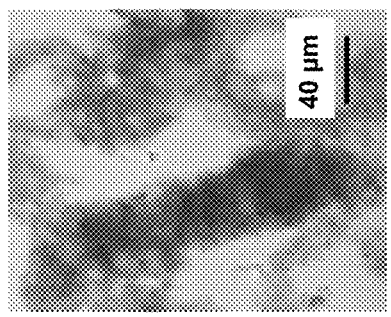
Figure 1:
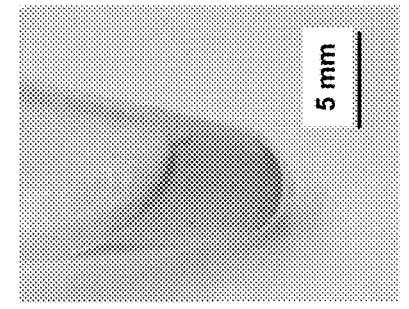
Figure 1:
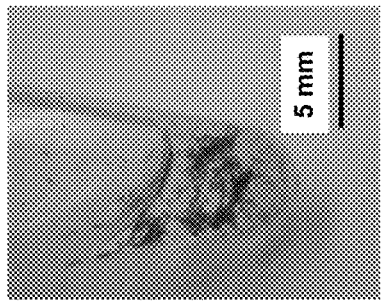
Figure 1:
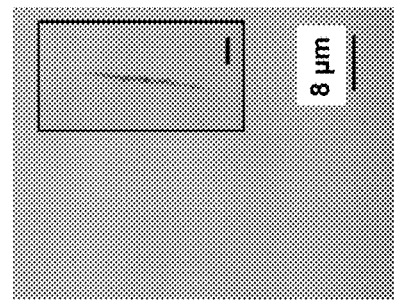

In select embodiments of the present invention a method for aggregating carbon nanotubes to permit scaling for manufacture of macro-scale items comprises: functionalizing single-wall carbon nanotubes (SWNTs); performing ligation reactions using an adenosine triphosphate (ATP)-dependent, thermostable single strand DNA-ligase (ssDNA-ligase), such that the ligation reactions are initiated in a heated water bath; and terminating the reactions after a pre-specified period by cooling the water bath to room temperature.

In developing select embodiments of the present invention, high-purity SWNTs derived from catalytic chemical vapor deposition (CVD) were purchased from Nanostructured & Amorphous Materials, Inc., Houston, Tex. These consist of 95% CNTs and 90% SWNTs. Oligonucleotides were purchased from Invitrogen, Carlsbad, Calif. ssDNA-ligase (CircLigase) was purchased from Epicentre Biotechnologies, Madison, Wis. DNase I was obtained from New England BioLabs, Beverly, Mass. All other chemicals, reagents, and supplies were obtained from major chemical suppliers and were of the highest quality and purity obtainable.

SWNTs were functionalized with single-stranded 30-mer polythymine oligonucleotides ($d(T)_{30}$) by ultra-sonication. 0.3 mg of SWNTs and 0.15 mg of desalted $d(T)_{30}$ were combined in 30 mM NaCl (total volume 0.5 mL). The ssDNA/SWNT mixture was sonicated continually with a CPX 130 Ultrasonic Processor (Cole Parmer, Vernon Hills, Ill.) at 75 W for three hrs in a 1 L water bath. Ice was added periodically to the water bath to maintain 4° C. After sonication, samples were centrifuged at 14,000 g for five hrs to remove insoluble CNTs. The degree of functionalization was estimated by subtracting the dried pellet weight from the original weight. After centrifugation, the supernatant was decanted and the absorbance was read at 730 nm as a measurement of CNT dispersal. Ten separate 0.5 mL DNA-functionalization reactions were performed and centrifuged as describe above. After centrifugation, supernatants were pooled into one fraction, which was used in all subsequent experiments. Potentially unbound ssDNA was removed using a 7 kDa molecular weight cutoff Slide-A-LyzerDialysis Cassette from Pierce Biotechnology, Inc., Rockford, Ill. Free DNA within the diffused fractions was quantified using an Invitrogen Quant-iT ssDNA assay kit.

Ligation reactions were performed using adenosine triphosphate (ATP)-dependent, thermostable ssDNA-ligase (CircLigase). CircLigase was chosen for its unique ability to proficiently link ssDNA having free 5'-phosphate and 3'-hydroxyl groups by intermolecular phosphodiester bonding. Ligation reactions were performed with the following parameters: 5 µL of purified DNA-functionalized SWNTs, 2 µL of 10× ligase buffer (Epicentre Biotechnologies), 2 µL of 1 mM ATP, and 2 µL of CircLigase (200 U). The final reaction volume was 20 µL in molecular-grade water. Reactions were initiated by incubation in a 60° C. water bath. After one hour reactions were terminated by cooling to room temperature. Controls included ligase-un-amended reactions and ATP-un-amended reactions. Five reactions were performed under each condition and pooled for subsequent analysis. The CNT aggregate size and distribution were estimated using a Nikon Eclipse E400 light microscope, Melville, N.Y., equipped with a Diagnostic Instruments, Inc. Insight digital camera and Spot™ imaging software, Sterling Heights, Mich.

To test the degree of DNA dissociation due to the enzymatic reaction temperature, 150 µL of the purified DNA-functionalized SWNTs was added to 150 µL of molecular-grade water and incubated at 40, 60, 80, and 100° C. for one hour. The samples were allowed to cool to room temperature and were centrifuged at 14 000 g for 30 min. Absorbance readings at 730 nm were taken prior to incubation and on the supernatant after centrifugation as a measurement of DNA dissociation.

Non-magnified bulk ligation reactions were imaged using a Canon PowerShot® G5 digital camera, Canon USA, Lake Success, N.Y. Magnified images were obtained during Raman analysis as described below and with wet-cell transmission electron microscopy (TEM). Wet-cell TEM was performed using a JEOL 2010 LaB6 TEM, Tokyo, Japan with a beam acceleration voltage of 200 keV. Franks, R. et al., *Nanosci. Nanotechnol.* 8, 4404, (2008).

Raman spectra and associated images were recorded using a Jobin Yvon LabRam HR 800 microRaman with 633 nm laser excitation and air objectives (both 10× and 50×), providing a spot size of 7-36 µm in this work. Images were captured with a digital charge-coupled device (CCD) camera. Wave number calibration was performed using the 521 $cm^{-1}$ emission of silica slides used for analysis. Approximately 10 µL of each experimental sample was spotted onto a silica substrate, and the laser was focused at both 10× and 50× long lenses using a laser power of 10 mW and spectra were collected from 100 to 3000 $cm^{-1}$. Raman spectra obtained were for qualitative purposes only.

On the basis of a literature review, polythymine (d(T)30, d(T)60, and d(T)90) and polyguanine thymine (d(GT)30, d(GT)60, and d(GT)90) oligonucleotide sequences were evaluated for their ability to disperse SWNTs in aqueous solution. Consistent with published reports, d(T)30 oligonucleotides were routinely found to disperse the maximum number of CNTs on the basis of the spectroscopic absorbance at 730 nm. Post-centrifugation weight measurements established that approximately 30-40% of the CNTs were dispersed into solution in the presence of oligonucleotides, which was also consistent with published data. Zheng (2003a). In an attempt to increase ssDNA ligase activity toward bonding only free 5'- and 3'-oligonucleotides on functionalized CNTs, dialysis was performed to remove unbound ssDNA and concentrate the samples twofold. However, nucleotides were not detected in the diffused fractions, suggesting that all oligonucleotides were bound to the CNTs. When the DNA-functionalized SWNTs were incubated in the presence of ATP and ssDNA-ligase, macroscopic aggregates, clearly visible without magnification, were readily formed as shown in FIG. 1A. The aggregates were random in size with the majority measuring several millimeters in length and diameter. When observed under 10× magnification, most of the larger aggregates appeared to be interconnected to one another by smaller, less dense aggregates as shown in FIG. 1B. In contrast, no macroscopic aggregates were observed in reactions lacking ligase as shown in FIG. 1C or ATP (data not shown). On the basis of microscopic analysis, most of the control reaction contained no visible SWNT aggregates when viewed under 50× magnification as shown in FIG. 1D. A small number of random SWNT bundles measuring less than 2 µm in width were observed as shown in the inset in FIG. 1D. These were estimated to be less than 5% of the aggregate formation in the ligase-amended reactions shown in FIG. 1A. The functionalization of CNTs with DNA is sensitive to physical parameters such as temperature and CNT radius. Gao, H., and Y. Kong, *Ann. Rev. Mater. Res.* 34, 123, (2004); Enyashin, A. N., et al., *Nanotechnology* 18, 245702, (2007). Confirmed by incubating functionalized SWNTs at various temperatures, formation of the small CNT bundles in the un-amended control reactions (no ligase) is due to a loss of DNA functionalization. Incubation at 60° C. reduced the absorbance at 730 nm by 5.0±0.4%, the amount estimated to have precipitated in the control. Increasing temperature to 80 and 100° C. reduced absorbance by 38.2±0.1 and 76.1±0.1%, respectively. Thus, small aggregates formed within the control were due to loss of functionality. In the presence of DNase I, the size of the ligase-mediated aggregates was reduced significantly as shown in FIG. 1E. After a ten minute treatment, average aggregate size was reduced roughly 100- to 200-fold and junctions between larger aggregates were completely eliminated as shown in FIG. 1F. Small aggregates (2 to 4 µm) remained. The enzymatic specificity of DNase I toward phosphodiester bond cleavage within polynucleotide chains demonstrated that SWNT aggregates were the result of DNA linkages.

Figure 2:
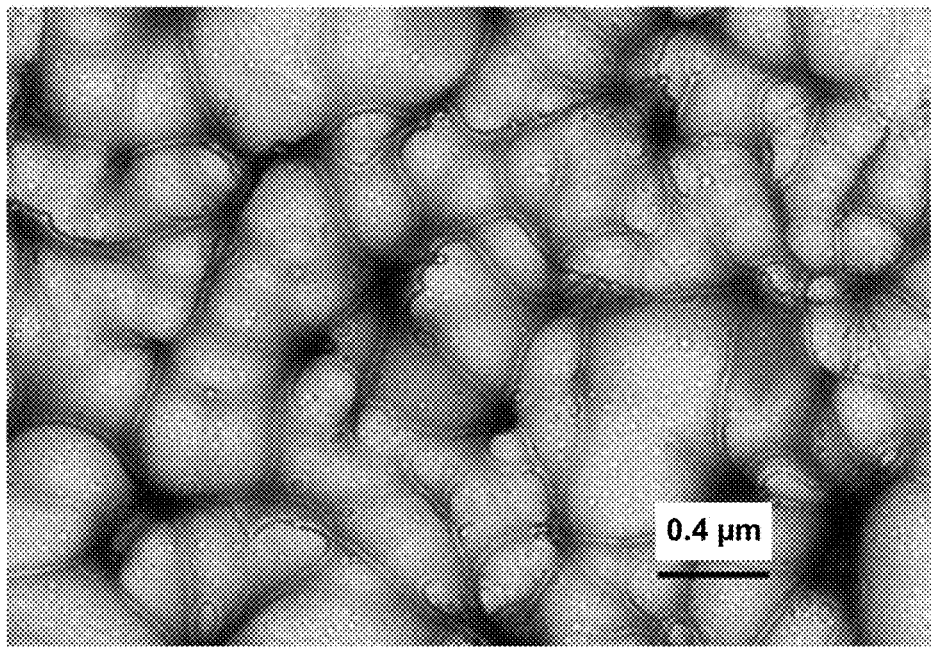
FIG. 2A is a photograph of a wet-cell TEM of ligated ssDNA-functionalized SWNTs.
FIG. 2B is a photograph of a wet-cell TEM of a controlled reaction of SWNTs without addition of a ligase.
Figure 2:
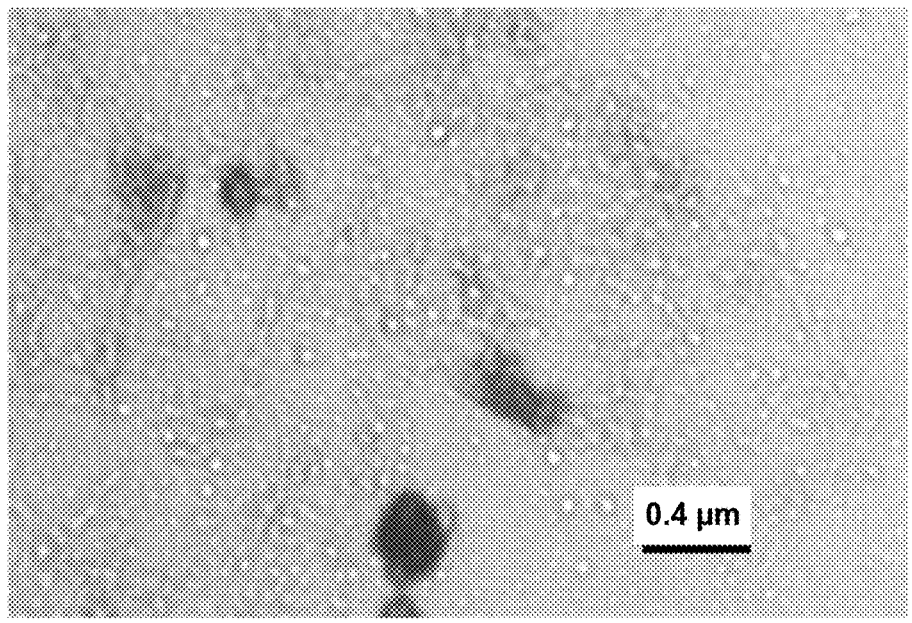

In addition to macroscopic and microscopic analysis, reactions were characterized by wet-cell TEM. Enzymatic-mediated aggregates were found to consist of a lattice-like structure where CNTs appeared to be radially bound to themselves and adjacent CNTs as shown in FIG. 2A. Many of the CNTs formed small loop structures, and others seemed to be bound to other CNTs, forming a 3D network. Neither structure was detected in reactions lacking ligase as shown in FIG. 2B. Most of the control reaction was composed of randomly dispersed SWNTs; however, some small, tightly bound CNT aggregates were observed. These are most likely formed via a loss of ssDNA functionality incurred during incubation, the imaging process, or both.

Figure 3:
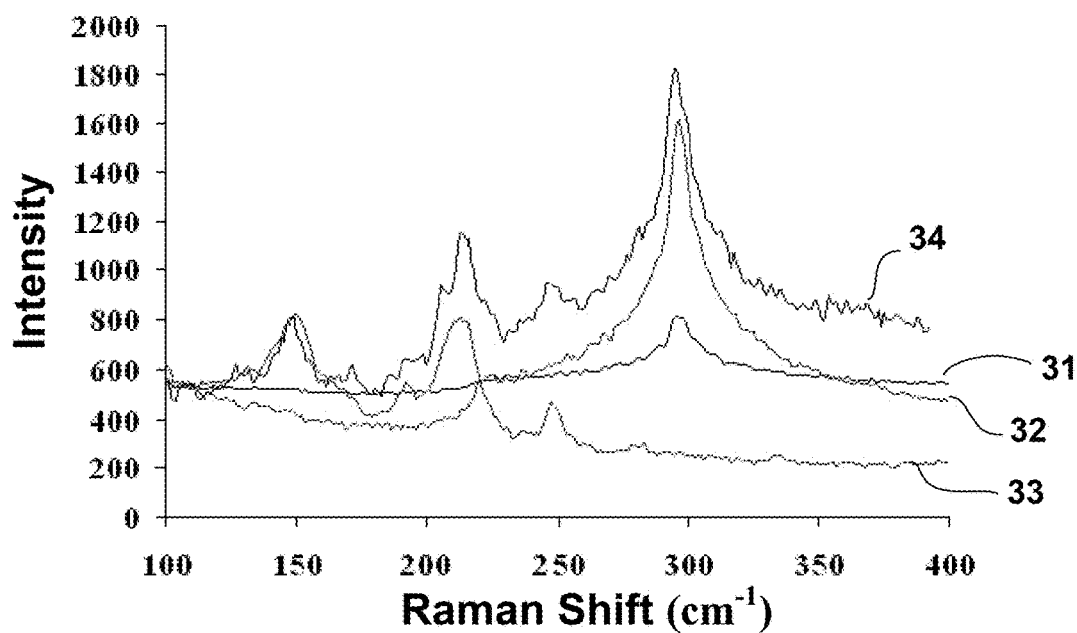
FIG. 3 depicts a Raman spectroscopic analysis of ligated DNA-functionalized SWNTs at a 633 nm excitation wavelength, representing a radial breathing mode.
Figure 4:
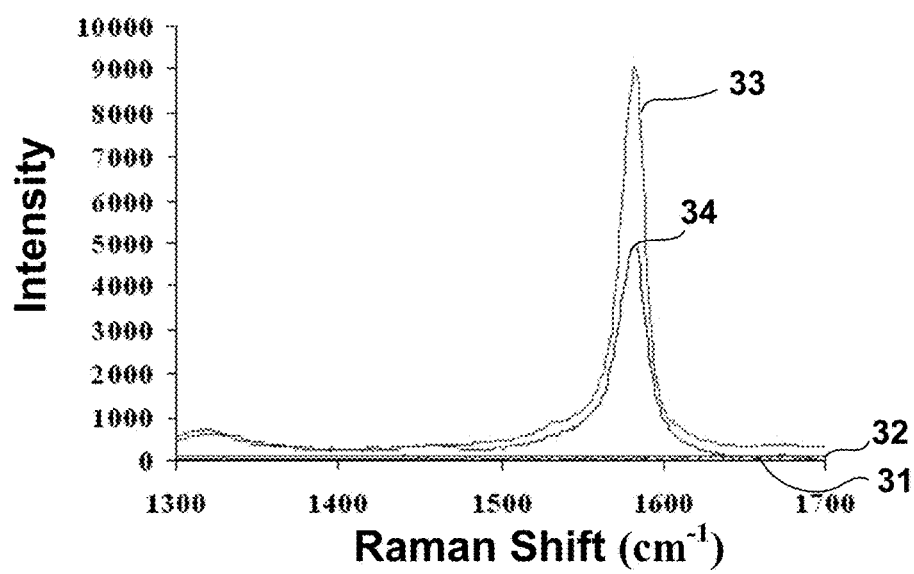
FIG. 4 depicts a Raman spectroscopic analysis of ligated DNA-functionalized SWNTs at a 633 nm excitation wavelength, representing G band.
Figure 5:
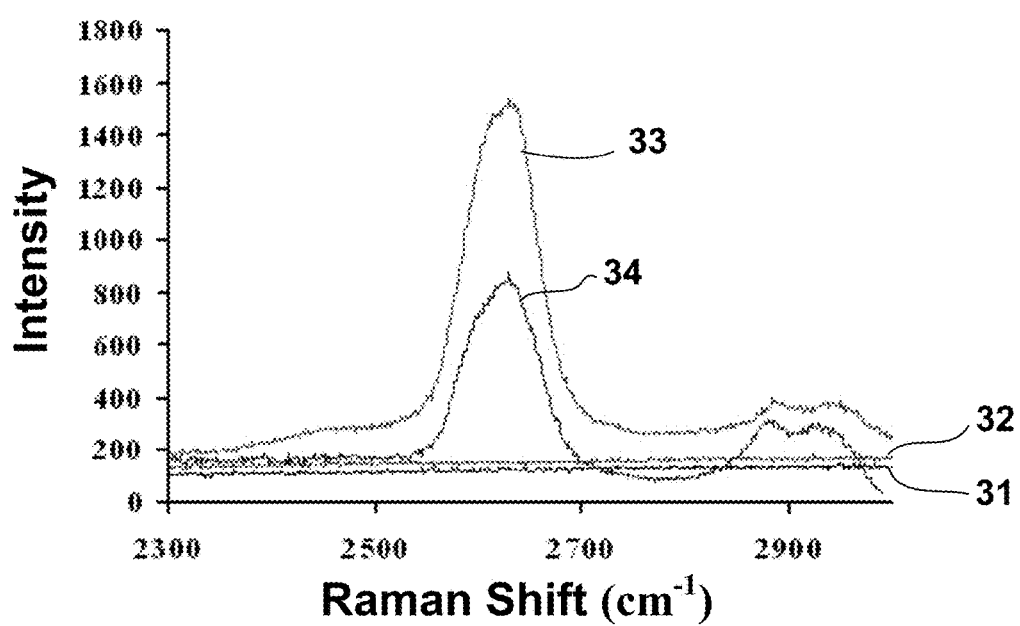
FIG. 5 depicts a Raman spectroscopic analysis of ligated DNA-functionalized SWNTs at a 633 nm excitation wavelength, representing G' band.

Reactions were further characterized by Raman spectroscopy analysis for qualitative purposes. Refer to FIG. 3. Spectroscopy was performed and no Raman spectra were observed in the DNA-functionalized SWNTs 31 or un-amended controls (no ligase) 32. Prominent spectra indicative of CNTs were observed in radial breathing mode (RBM) for ligase-amended reactions 33 and endonuclease-treated reactions 34 as shown in FIG. 3; in G-band as shown in FIG. 4, and in G'-band as shown in FIG. 5. Dresselhaus (2004).

Figure 6:
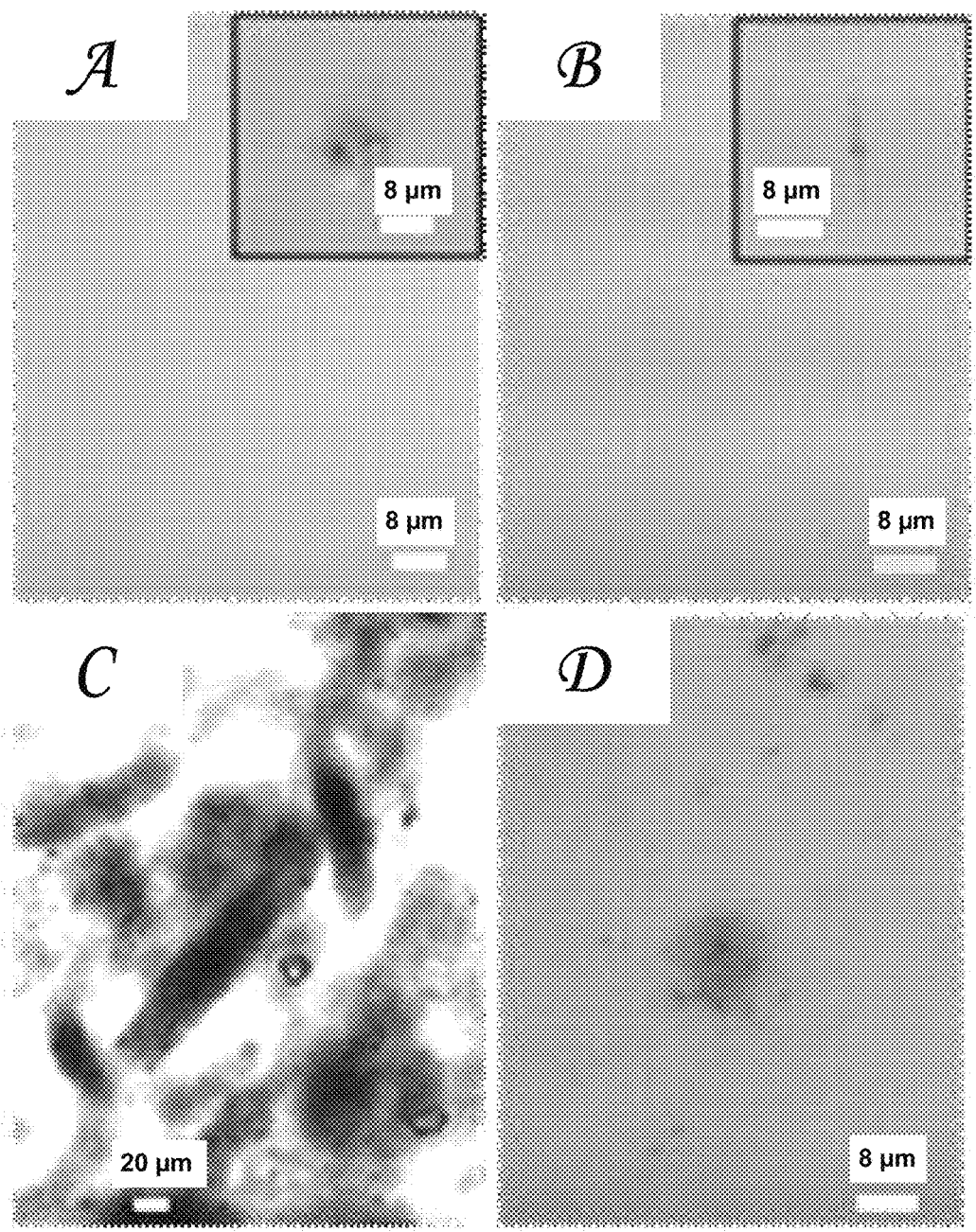
FIG. 6A is a light microscope image of DNA-functionalized SWNTs.
FIG. 6B is a light microscope image of DNA un-amended SWNTs (no ligase).
FIG. 6C is a light microscope image of DNA ligase-amended SWNTs.
FIG. 6D is a light microscope image of DNA ligase-amended SWNTs after deoxyribonuclease treatment.

Corresponding light microscope images are shown in FIGS. 6 A-D. The laser was focused on the centers of images in FIGS. 6 A-C and on the darkest region in FIG. 6D. The lack of spectra in the DNA-functionalized SWNTs 31 and un-amended controls 32 is due to the uniform dispersion of the SWNTs, resulting in low CNT concentrations at the point of laser excitation. Intense Raman spectra were observed in RBM (FIG. 3), in G- (FIG. 4) and in G'-bands (FIG. 5) in the reactions containing ligase because of large aggregate formation. Deoxyribonuclease treatment lowered the Raman spectral intensities significantly in both the G-band (FIG. 4) and the G'-band (FIG. 5). Intensities decreased roughly twofold and can be associated with a reduction in SWNT aggregate size as determined by light microscopy.

These data show that SWNT aggregation is due to ATP-dependent 5', 3'-phosphodiester enzymatic activity. The lack of aggregation in the absence of ligase and ATP confirms that aggregate formation is not due to physical means such as the loss of DNA functionality, protein binding, or ionic changes caused by reaction buffer constituents, and the like. Dispersal of aggregates using DNase I demonstrates that structures were formed by DNA linkage.

When DNA-functionalized CNTs were incubated with ssDNA-ligase, the formation of macroscopic aggregates was observed and confirmed by multiple methods as described above. Aggregate formation was not observed in reactions lacking enzyme or ATP, indicating enzymatic mediation. The addition of deoxyribonuclease to the ligated reactions visibly reduced aggregate dimensions as well as Raman intensity in the G- and G'-bands. This indicates that assimilation of DNA-functionalized SWNTs is due to 5', 3'-enzymatic phosphodiester bonding.

The abstract of the disclosure is provided to comply with the rules requiring an abstract that will allow a searcher to quickly ascertain the subject matter of the technical disclosure of any patent issued from this disclosure. (37 CFR § 1.72(b)). Any advantages and benefits described may not apply to all embodiments of the invention.

While select embodiments of the present invention have been described, those skilled in the art will recognize that the invention can be practiced with modifications within the spirit and scope of the appended claims. For example, although the system is described in specific examples for aggregating SWNTs, it may be used for aggregating any type of CNTs that may be useful in such diverse applications as structural, mechanical, chemical, and electrical applications, and the like. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Thus, it is intended that all matter contained in the foregoing description or shown in the accompanying drawings shall be interpreted as illustrative rather than limiting, and the invention should be defined only in accordance with the following claims and their equivalents.

We claim:

1. A method for aggregating CNTs to permit scaling for manufacture of macro-scale items, comprising: functionalizing SWNTs; performing ligation reactions using an adenosine triphosphate (ATP)-dependent, thermostable ssDNA-ligase, wherein said ligation reactions are initiated in a heated water bath; and terminating said reactions after a pre-specified period by cooling said water bath to room temperature; and wherein said SWNTs are functionalized with single-stranded 30-mer polythymine oligonucleotides $(d(T)_{30})$ by ultra-sonication.

2. The method of claim 1 centrifuging said SWNTs to remove insoluble CNTs.

3. The method of claim 1 removing potentially unbound said ssDNA.

4. The method of claim 1 performing ligation reactions using: purified DNA-functionalized SWNTs, 10× ligase buffer, 1 mM ATP, said ssDNA-ligase, and molecular-grade water.

5. The method of claim 4 initiating said reactions by incubating in a water bath at a temperature of approximately 30° C. to approximately 100° C.

6. The method of claim 4 initiating said reactions by incubating in a water bath at a temperature of approximately 60° C.

7. The method of claim 5 terminating said reactions after approximately one hour by cooling to room temperature.

* * * * *